United States Patent
Yamaguchi et al.

(10) Patent No.: US 10,265,004 B2
(45) Date of Patent: Apr. 23, 2019

(54) BLOOD INFORMATION MEASURING APPARATUS AND METHOD

(75) Inventors: Hiroshi Yamaguchi, Kanagawa (JP); Takaaki Saito, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 1248 days.

(21) Appl. No.: 13/533,882

(22) Filed: Jun. 26, 2012

(65) Prior Publication Data
US 2013/0018242 A1    Jan. 17, 2013

(30) Foreign Application Priority Data
Jul. 14, 2011 (JP) .................... 2011-155611

(51) Int. Cl.
A61B 5/1459    (2006.01)
A61B 5/1455    (2006.01)
(Continued)

(52) U.S. Cl.
CPC .......... A61B 5/14551 (2013.01); A61B 1/043 (2013.01); A61B 1/0638 (2013.01);
(Continued)

(58) Field of Classification Search
CPC .... A61B 5/0059; A61B 5/0084; A61B 5/0066
(Continued)

(56) References Cited

U.S. PATENT DOCUMENTS 5,001,556 A * 3/1991 Nakamura ......... A61B 1/00009
348/70
6,350,261 B1 * 2/2002 Domankevitz ........ A61B 18/20
606/17
(Continued)

FOREIGN PATENT DOCUMENTS

JP    01-308531 A    12/1989
JP    06-315477 A    11/1994
(Continued)

OTHER PUBLICATIONS

Elas et al. Quantitative Tumor Oxymetric Images From 4D Electron paramagnetic resonance imaging (EPRI): Methodology and comparison with blood oxygen level-dependent (BOLD) MRI. 2003 Mag.Res.Med. 49:682-691.*
(Continued)

Primary Examiner — Tse Chen
Assistant Examiner — Patrick M Mehl
(74) Attorney, Agent, or Firm — McGinn I.P. Law Group, PLLC.

(57) ABSTRACT

In a blood information measuring apparatus, a plurality of types of light of a superficial layer wavelength set, a middle layer wavelength set, and a deep layer wavelength set are successively applied to a detected hypoxic region. A CCD captures an image under the light of each wavelength set, and an oxygen saturation image is produced independently from one wavelength set to another. A wavelength set determination section creates a histogram of each oxygen saturation image. The wavelength set determination section chooses one of the wavelength sets corresponding to the histogram having a maximum variance as an actual imaging wavelength set. Actual imaging operation is performed using the actual imaging wavelength set, and an oxygen saturation level of each pixel is calculated. The oxygen saturation level is reflected in the image, and the image is displayed on a monitor.

13 Claims, 11 Drawing Sheets

(51) Int. Cl.
*A61B 1/06* (2006.01)
*A61B 1/04* (2006.01)
*A61B 5/00* (2006.01)

(52) U.S. Cl.
CPC .......... *A61B 1/0646* (2013.01); *A61B 5/0037* (2013.01); *A61B 5/0084* (2013.01); *A61B 5/489* (2013.01); *A61B 5/1459* (2013.01)

(58) Field of Classification Search
USPC ................... 600/473, 476, 477, 478, 339
See application file for complete search history.

(56) References Cited

U.S. PATENT DOCUMENTS

| | | | |
|---|---|---|---|
| 6,905,492 B2* | 6/2005 | Zvuloni | A61B 8/0833 606/21 |
| 7,627,363 B2* | 12/2009 | Yaroslavsky | A61B 5/0059 600/407 |
| 2003/0206272 A1* | 11/2003 | Cornsweet et al. | 351/206 |
| 2008/0281154 A1 | 11/2008 | Gono et al. | |
| 2009/0137908 A1* | 5/2009 | Patwardhan | A61B 5/0059 600/476 |
| 2009/0318761 A1* | 12/2009 | Rabinovitz | A61B 1/042 600/118 |
| 2010/0036260 A1* | 2/2010 | Zuluaga | A61B 1/00142 600/476 |
| 2011/0144462 A1* | 6/2011 | Lifsitz | A61B 5/0059 600/336 |

FOREIGN PATENT DOCUMENTS

| | | |
|---|---|---|
| JP | 2000-262459 A | 9/2000 |
| JP | 2002-058631 A | 2/2002 |
| JP | 3583731 B2 | 11/2004 |
| JP | 2010-087617 A | 4/2010 |

OTHER PUBLICATIONS

Vaupel et al. Blood flow oxygen and nutrient supply and metabolic microenvironment of human tumors: A review. 1989 Cancer Res. 49:6449-6465.*
Bard et al. 2005 Am. J. Respir. Crit. Care Med. 171:1178-1184.*
Brown et al. Quantitative Optical Spectroscopy a Robust Tool for Direct Measurement of Breast Cancer Vascular Oxygenation and Total Hemoglobin Content in Vivo. 2009 Cancer Res. 69:2919-2926.*
Fawzy Quantification of mucosa oxygenation using three discrete spectral bands of visible light. 2009 J.Biophoton. 2:744-749.*
Gheorghe Narrow-Band Imaging Endoscopy for Diagnosis of Malignant and Premalignant Gastrointestinal Lesions. 2006 J. Gastrointest. Liver Dis. 15:77-82.*
Lambert et al. Narrow-band imaging in digestive endoscopy. 2007 TheScientificWorldJOURNAL 7:449-465—Special Issue: Recent Advances in Gastrointestinal Imaging.*
Maxim et al. Optical detection of tumors in vivo by visible light tissue oximetry. 2005 Technol.Cancer Res. Treat. 4 227-234.*
Dipen Rana Integration of hyperspectral imaging system for optimized data acquisition and control to revolutionize pathology applications. 2008 University of Texas at Arlington PhD thesis p. 27.*
Shibuya et al. High magnification bronchovideoscopy combined with narrow band imaging could detect capillary loops of angiogenic squamous dysplasia in heavy smokers at high risk for lung cancer. 2003 Thorax 58:989-995.*
Yoshida et al. Narrow-band imaging system with magnifying endoscopy for superficial esophageal leasions. 2004 Gastrointestinal Endoscopy 59:288-295.*
Extended European Search Report dated Oct. 22, 2012.
Japanese Office Action dated Apr. 24, 2013 and English translation thereof.

* cited by examiner

| DEPTH | WAVELENGTH SET (nm) |
|---|---|
| SUPERFICIAL LAYER | 405、445 |
| MIDDLE LAYER | 473、WHITE LIGHT |
| DEEP LAYER | 630、780 |

82

BLOOD INFORMATION MEASURING APPARATUS AND METHOD

BACKGROUND OF THE INVENTION

1. Field of the Invention

The present invention relates to a blood information measuring apparatus and method for measuring blood information from an image signal of a blood vessel.

2. Description Related to the Prior Art

Endoscopes are widely used for observation of a lesion located inside a human body. The endoscope is provided with an insert section to be introduced into the human body, and a handling section for steering the insert section. The insert section has a lighting window and an imaging window at its distal end. An internal body portion is imaged through the imaging window, while being illuminated with light through the lighting window. An obtained endoscopic image is displayed on a monitor.

As a light source of the endoscope, a white light source such as a xenon lamp or a metal halide lamp is conventionally available. Additionally, there is a method recently in the limelight in which light (narrow band light) of a narrow wavelength band is used as illumination light to facilitate finding out the lesion (refer to US Patent Application Publication No. 2008/0281154 corresponding to Japanese Patent No. 3583731).

Also, there is studied a method for measuring information of blood flowing through a blood vessel, for example, an oxygen saturation level of hemoglobin, a blood flow rate, and the like (refer to Japanese Patent Laid-Open Publication No. 06-315477). In this method, the blood vessel is extracted from the endoscopic image captured under the narrow band light, and the blood information is obtained from an image signal. This method uses the illumination light in wavelength bands of 300 to 400 nm, around 400 nm, 400 to 500 nm, 500 to 600 nm, 450 to 850 nm, and the like. Taking the case of measuring the oxygen saturation level of hemoglobin as an example, an optimal wavelength band is chosen from the five wavelength bands in accordance with the body portion. Each wavelength band has a pair of wavelengths as a wavelength set. The pair includes a measurement wavelength at which absorbance much varies with the oxygen saturation level and a reference wavelength at which the absorbance hardly varies therewith. Two types of light having the measurement and reference wavelengths are applied to the body portion in succession, to obtain a measurement image signal taken under the measurement light and a reference image signal taken under the reference light. The measurement image signal varies based on difference in the absorbance, so the measurement image signal is corrected with the reference image signal to obtain the oxygen saturation level of blood flowing through the blood vessel.

By the way, how deep light penetrates into human tissue depends on a wavelength band of the light. Taking advantage of this property, the depth of a lesion such as cancer can be inspected. More specifically, switching among the wavelength sets makes it possible to measure the oxygen saturation level of blood flowing through blood vessels in different depths from a mucosal layer to a submucosal layer. This allows inspection of the stage of the cancer.

The Japanese Patent Laid-Open Publication No. 06-315477 does not specifically disclose switching timing of the wavelength sets. Furthermore, some types of cancer such as scirrhous carcinoma (linitis plastica) do not manifest themselves in a surface of the mucosal layer, but occur in the middle of the mucosal layer (see FIG. 15). Therefore, the wavelength set suitable for diagnosis differs according to which body portion is to be examined. If the switching among all the wavelength sets is automatically performed, the wavelength sets unnecessary for the diagnosis are inevitably used, resulting in wasted time and effort. If a doctor manually performs the switching, complicated operation is required.

SUMMARY OF THE INVENTION

An object of the present invention is to provide a blood information measuring apparatus and method that can automatically choose a wavelength set suitable for diagnosis.

To achieve the above and other objects of the present invention, a blood information measuring apparatus according to the present invention includes a lighting section, an imaging section, a wavelength tunable element, a blood information calculation section, a monitor, a wavelength set switching section, a wavelength set determination section, and a control section. The lighting section applies illumination light to a body portion having a blood vessel. The imaging section performs photoelectric conversion of reflected light from the body portion irradiated with the illumination light and outputs an image signal. The wavelength tunable element narrows a wavelength band of the illumination light to be applied to the body portion or the reflected light to be incident on the imaging section. The blood information calculation section calculates blood information based on the image signal. The monitor displays the blood information. The wavelength set switching section drives the wavelength tunable element to switch among a plurality of wavelength sets. Each wavelength set includes a plurality of types of light that penetrate to a similar depth into the body portion. The wavelength set determination section chooses one of the wavelength sets as an actual imaging wavelength set to be used in actual imaging operation based on the image signal obtained in preliminary imaging operation. The control section performs the preliminary imaging operation and the actual imaging operation. In the preliminary imaging operation, preliminary images are captured while the wavelength set switching section switches among the wavelength sets. In the actual imaging operation, an actual image is captured with use of the actual imaging wavelength set.

The blood information is preferably an oxygen saturation level of hemoglobin. The wavelength set determination section preferably creates a histogram of the oxygen saturation level of each preliminary image independently from one wavelength set to another, and determines the actual imaging wavelength set based on the histograms. One of the wavelength sets corresponding to the histogram having a maximum variance or a maximum standard deviation is preferably chosen as the actual imaging wavelength set.

The blood information measuring apparatus may further include a blood vessel area determination section for determining a blood vessel area from the image signal. The wavelength set determination section calculates difference between a mean value of the oxygen saturation level of the blood vessel area and that of another area independently from one wavelength set to another, and chooses one of the wavelength sets having a maximum value of the difference as the actual imaging wavelength set. In another case, the wavelength set determination section calculates density of the blood vessels in the blood vessel area independently from one wavelength set to another, and chooses one of the wavelength sets having a maximum value of the density as the actual imaging wavelength set. In further another case, the wavelength set determination section may calculate a mean value of the oxygen saturation level independently from one wavelength set to another, and chooses one of the wavelength sets having a maximum value of the mean value as the actual imaging wavelength set.

The blood information measuring apparatus may further include a binning processing section for applying a binning process to the image signal obtained in the preliminary imaging operation.

The wavelength set switching section may choose one of the wavelength sets as an abnormality detection wavelength set. If a mean value of the oxygen saturation level obtained with the abnormality detection wavelength set is less than a threshold value, the control section starts the preliminary imaging operation.

One of the wavelength sets may be a superficial layer wavelength set having a plurality of types of narrow band light in a blue wavelength band. The superficial layer wavelength set may be used as the abnormality detection wavelength set.

The blood information measuring apparatus may further include a location detecting section for detecting a location of the body portion in a body cavity. The abnormality detection wavelength set may be chosen in accordance with the location. The location detecting section may detect the location of the body portion in the body cavity through an image recognition technique.

The plurality of wavelength sets may include a superficial layer wavelength set having a plurality of types of narrow band light in a blue wavelength band, and a middle layer wavelength set having a plurality of types of narrow band light in a green wavelength band. If the location detecting section detects that the body portion is in esophagus or large intestine, the superficial layer wavelength set is chosen as the abnormality detection wavelength set. If the location detecting section detects that the body portion is in stomach, the middle layer wavelength set is chosen as the abnormality detection wavelength set.

The lighting section may emit white light having a broad wavelength band as the illumination light. The wavelength tunable element may be disposed in the lighting section to narrow a wavelength band of the illumination light. In another case, the wavelength tunable element may be disposed in the imaging section to narrow a wavelength band of the reflected light from the body portion irradiated with the illumination light.

The plurality of wavelength sets may include a superficial layer wavelength set having a plurality of types of narrow band light in a blue wavelength band, a middle layer wavelength set having a plurality of types of narrow band light in a green wavelength band, and a deep layer wavelength set having a plurality of types of narrow band light in a red wavelength band.

The blood information measuring apparatus may further include a mode switching section for switching between a normal mode and a special mode. In the normal mode, white light having a broad wavelength band is applied to the body portion, and an image produced from the image signal obtained under the white light is displayed on the monitor. In the special mode, the preliminary imaging operation and the actual imaging operation are carried out. The image of the body portion is colored based on the oxygen saturation level of each pixel obtained in the actual imaging operation, and the colored image is displayed on the monitor.

A blood information measuring method includes the steps of applying illumination light to a body portion having a blood vessel; performing photoelectric conversion of reflected light from the body portion irradiated with the illumination light and outputting an image signal; narrowing a wavelength band of the illumination light to be applied to the body portion or the reflected light to be incident on an imaging section in accordance with one of a plurality of wavelength sets; calculating blood information based on the image signal; carrying out preliminary imaging operation by switching among the plurality of wavelength sets, each of which includes a plurality of types of narrow band light penetrating to a similar depth into the body portion; choosing one of the wavelength sets as an actual imaging wavelength set to be used in actual imaging operation based on the image signal obtained in the preliminary imaging operation; carrying out the actual imaging operation with use of the actual imaging wavelength set; and displaying on a monitor the blood information measured in the actual imaging operation.

According to the present invention, the preliminary imaging operation is carried out with successive switching among the plurality of wavelength sets, and the wavelength set to be used in the actual imaging operation is determined based on the image signals obtained in the preliminary imaging operation. Therefore, it is possible to automatically choose the wavelength set suitable for diagnosis, and efficiently measure the blood information.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
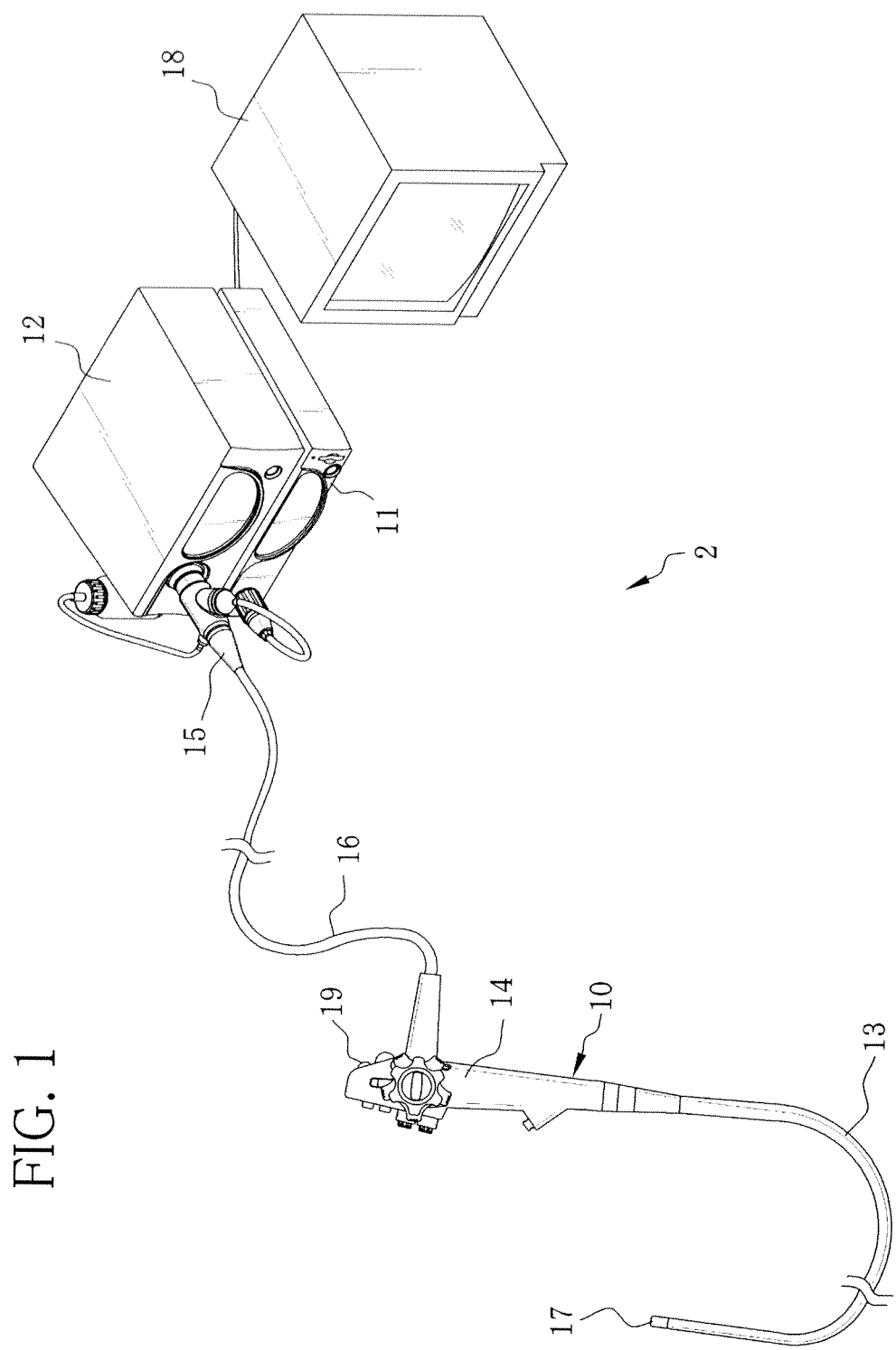
FIG. 1 is an external view of a blood information measuring apparatus.

As shown in FIG. 1, a blood information measuring apparatus 2 is constituted of an electronic endoscope 10, a processor device 11, and a light source device 12. The blood information measuring apparatus 2 measures blood information as biological information. As is widely known, the electronic endoscope 10 includes a flexible insert section 13 to be introduced into a patient's body cavity, a handling section 14 coupled to a proximal end of the insert section 13, a connector 15 connected to the processor device 11 and the light source device 12, and a universal cord for connecting between the handling section 14 and the connector 15. Note that, the blood information measuring apparatus 2 is identical to a well-known electronic endoscope apparatus, except that an image processor and a CPU of the processor device 11 have the additional function of measuring blood information.

The handling section 14 is provided with various operation members, including an angle knob for flexibly bending a distal end portion 17 of the insert section 13 upward and downward and from side to side, an air/water supply button for ejecting air and water from an air/water supply nozzle, a release button for capturing a still observation image (endoscopic image), and the like.

The handling section 14 has a medical instrument inlet on its front end side. Into the medical instrument inlet, a medical instrument such as a forceps or an electric cautery is inserted. The medical instrument inlet is coupled to a medical instrument outlet provided at the distal end portion 17 through a channel provided in the insert section 13.

The processor device 11 is electrically connected to the light source device 12 with a cable, and performs centralized control of the blood information measuring apparatus 2. The processor device 11 supplies power to the electronic endoscope 10 through a transmission cable, which is run through the universal cord 16 and the insert section 13, and controls operation of a CCD 33 (see FIG. 2) provided at the distal end portion 17. The processor device 11 receives an image signal outputted from the CCD 33 through the transmission cable, and applies various processes to the received image signal to produce a picture signal. The picture signal produced in the processor device 11 is sent to a monitor 18 connected to the processor device 11 with a cable, so an observation image is displayed on a screen of the monitor 18.

The blood information measuring apparatus 2 has a normal mode for observing an internal body portion under illumination with white light, and a special mode for calculating blood information with application of narrow band light to the body portion. Mode switching is performed by operating a mode switch 19. The blood information measuring apparatus 2 is automatically put into the normal mode immediately after turning the power on by a command from the processor device 11.

Figure 2:
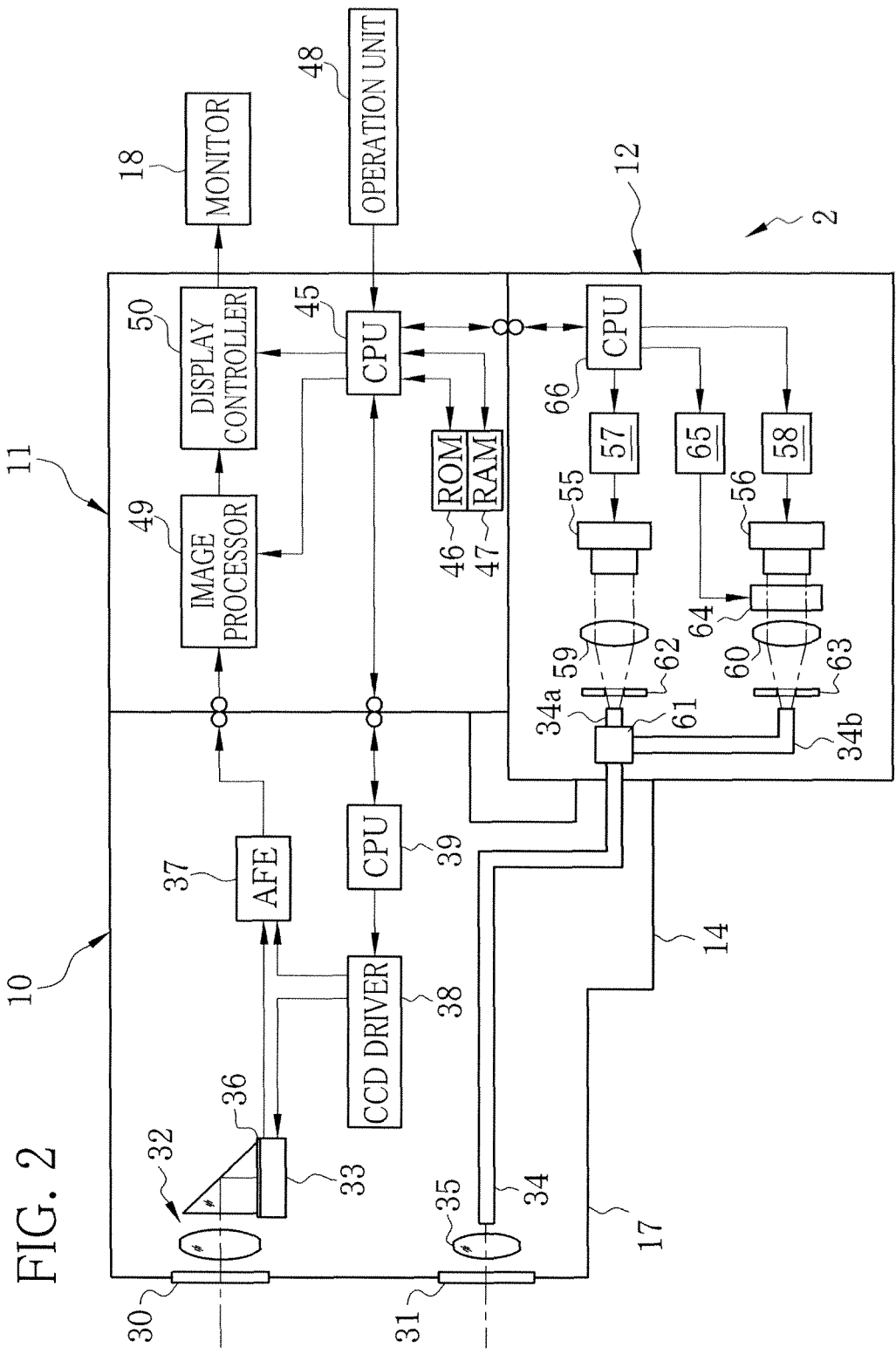
FIG. 2 is a block diagram of the blood information measuring apparatus.

In FIG. 2, the distal end portion 17 has an imaging window 30, a lighting window 31, and the like. The CCD 33 for imaging the inside of the body is disposed in the recess of the imaging window 30 through the medium of an objective optical system 32 including a lens group and a prism. Illumination light is emitted from the light source device 12 and guided through a light guide 34 routed through the universal cord 16 and the insert section 13, and is applied through a lighting lens 35 and the lighting window 31 to the body portion.

Figure 3:
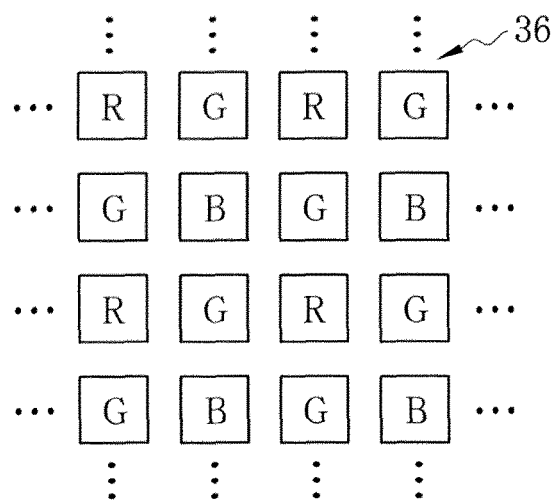
FIG. 3 is an explanatory view of a color filter of a Bayer arrangement.
Figure 4:
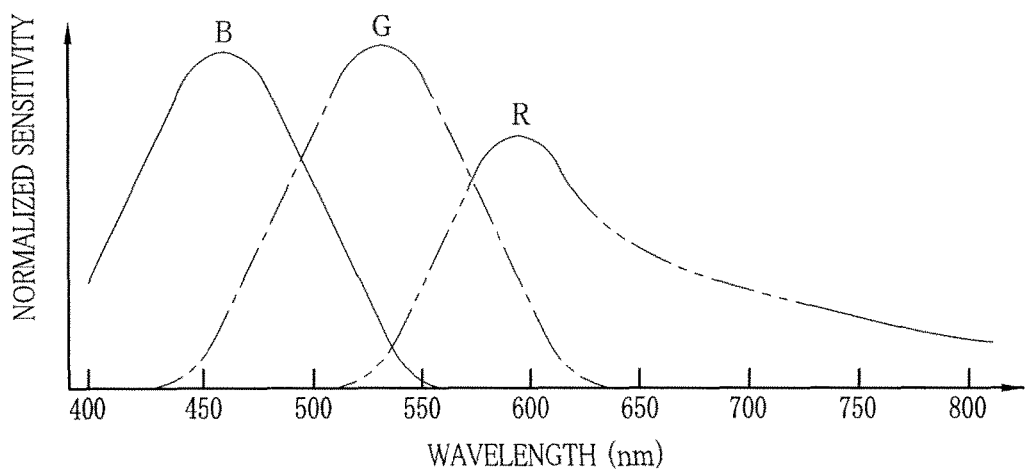
FIG. 4 is a graph showing sensitivity spectra of each of R, G, and B pixels of a CCD.

The illumination light is reflected from the body portion, and is incident on the COD 33 through the imaging window 30 and the objective optical system 32. The CCD 33 performs photoelectric conversion of the reflected light, and outputs the image signal. In an imaging plane of the CCD 33, there is formed a color filter having a plurality of color segments, for example, a RGB (red, green, and blue) primary color filter 36 of a Bayer arrangement, as shown in FIG. 3. FIG. 4 shows sensitivity spectra of each of R, G, and B pixels of the CCD 33 ascribable to spectral transmittance of the primary color filter 36 and spectral sensitivity of the pixels themselves. The R pixel has a sensitivity peak in the vicinity of 600 nm. The G pixel has a sensitivity peak in the vicinity of 530 nm. The B pixel has a sensitivity peak in the vicinity of 460 nm. The R pixel has broad spectral sensitivity, and is sensitive to light having wavelengths even in an infrared range in the vicinity of approximately 1000 nm.

An analog frontend processor (AFE) 37 includes a correlated double sampling circuit (CDS), an automatic gain controller (AGC) and an analog-to-digital converter (A/D). The CDS applies a correlated double sampling process to the image signal outputted from the CCD 33, to remove reset noise and amplification noise occurring in the CCD 33. The AGC amplifies the image signal after the noise removal by the CDS with a gain (amplification factor) specified by the processor device 11. The A/D converts the image signal amplified by the AGC into a digital signal of a predetermined bit number. The image signal digitized by the A/D is inputted through the transmission cable to an image processor 49 of the processor device 11.

A CCD driver 38 generates drive pulses (vertical/horizontal scan pulse, electronic shutter pulse, readout pulse, reset pulse, and the like) of the CCD 33 and a synchronization pulse of the AFE 37. The CCD 33 carries out image capturing operation in response to the drive pulses from the CCD driver 38, and outputs the image signal. The AFE 37 operates based on the synchronization pulse from the CCD driver 38.

After the electronic endoscope 10 is connected to the processor device 11, a CPU 39 actuates the CCD driver 38 in response to an operation start command from a CPU 45 of the processor device 11, and adjusts the gain of the AGC of the AFE 37 through the CCD driver 38.

The CPU 45 performs centralized control of the entire processor device 11. The CPU 45 is connected to every part through a data bus, an address bus, and control lines (all not shown) A ROM 46 stores various programs (OS, application programs, and the like) and data (graphic data and the like) to control operation of the processor device 11. The CPU 45 reads out the necessary programs and the data from the ROM 46, and loads the programs to a RAM 47 being a working memory, and runs the programs in sequence. The CPU 45 also obtains information varying from examination to examination such as text data including an examination date, a patient's name, and a doctor's name from an operation unit 48 of the processor device 11 or through a network e.g. a LAN (local area network), and writes the information to the RAM 47.

The operation unit 48 is a well-known input device including an operation panel provided on a cabinet of the processor device 11, a mouse, and a keyboard. The CPU 45 performs preliminary imaging operation for choosing a wavelength set to be used in actual imaging operation, measurement of the blood information, and the like in response to operation signals from the operation unit 48 and from the release button and the mode switch 19 provided on the handling section 14 of the electronic endoscope 10.

The image processor 49 calculates the blood information, as described later in detail, in addition to subjecting the image signal inputted from the electronic endoscope 10 to various image processes such as color interpolation, white balance adjustment, gamma correction, image enhancement, image noise reduction, and color conversion.

A display controller 50 receives the graphic data from the ROM 46 and the RAM 47 through the CPU 45. The graphic data includes a display mask for covering an ineffective pixel area of the observation image to expose only an effective pixel area, the text data such as the examination date, the patient's name, the doctor's name, and an examination mode name chosen at the present time, a graphical user interface (GUI), and the like. The display controller 50 performs various display control processes. More specifically, the display controller 50 overlays the display mask, the text data, and the GUI on an image from the image processor 49, and draws the image after the overlaying process on the screen of the monitor 18.

The display controller 50 has a frame memory (not shown) for temporarily storing the image from the image processor 49. The display controller 50 reads out the image from the frame memory, and converts the read image into a video signal (component signal, composite signal, and the like) compatible with a display format of the monitor 18. Thus, the observation image is displayed on the monitor 18.

Besides the components described above, the processor device 11 is provided with a compression circuit for compressing the image in a predetermined compression format (for example, a JPEG format), a media I/F for writing the compressed image to a removable medium such as a CF card, a magneto-optical disk (MO), or a CD-R, a network I/F for controlling transmission of various types of data through a network such as the LAN, and the like. The compression circuit, the media I/F, and the network I/F are connected to the CPU 45 via the data bus.

The light source device 12 has a first light source 55 and a second light source 56. The first and second light sources 55 and 56 have identical structure, and have a xenon lamp, a halogen lamp, a white LED (light emitting diode), or the like that emits white light of a broad wavelength band extending from blue to red, from 400 nm to 800 nm, for example. Alternatively, as the first and second light sources 55 and 56, another light source may be used that emits the white light by mixing blue or ultraviolet excitation light emitted from a semiconductor laser with green to yellow to red fluorescence emitted from a phosphor by excitation.

The first and second light sources 55 and 56 are driven by light source drives 57 and 58, respectively. A condenser lens 59 gathers the light emitted from the first light source 55, and leads the light into a light guide 34a disposed on a light exit side of the first light source 55. A condenser lens 60 gathers the light emitted from the second light source 56, and leads the light into a light guide 34b disposed on a light exit side of the second light source 56. The light guides 34a and 34b are coupled to the single light guide 34 via a coupler 61. A variable aperture stop 62 is disposed between the condenser lens 59 and the light guide 34a to adjust the amount of light to be incident upon a light entrance of the light guide 34a, and a variable aperture stop 63 is disposed between the condenser lens 60 and the light guide 34b to adjust the amount of light to be incident upon a light entrance of the light guide 34b. Without using the coupler 61, each light source 55, 56 may be provided with a light guide, to transmit the light separately to the lighting window 31.

A wavelength tunable element 64 is disposed between the second light source 56 and the condenser lens 60. The wavelength tunable element 64 is driven by an element driver 65 to change a wavelength band of light to be transmitted therethrough. As the wavelength tunable element 64, an etalon is usable in which operation of an actuator e.g. a piezoelectric element varies a surface distance between two boards made of high reflective filters so as to control the wavelength band of the light to be transmitted. In another case, a liquid crystal tunable filter is usable in which a birefringent filter and nematic liquid crystal cells are disposed between a pair of polarizing filters, and varying an applied voltage to the liquid crystal cells controls the wavelength band of the light to be transmitted. In further another case, a rotary filter being a combination of a plurality of interference filters (band pass filters) may be used as the wavelength tunable element 64.

A CPU 66 of the light source device 12 communicates with the CPU 45 of the processor device 11. The CPU 66 performs turn-on and -off control of each individual light source 55, 56 and light amount control of each individual variable aperture stop 62, 63 through the light source driver 57, 58. Also, the CPU 66 controls the operation of the wavelength tunable element 64 through the element driver 65.

In the normal mode, the CPU 45 controls the operation of the light source driver 57 through the CPU 66 so as to turn on only the first light source 55. Thus, only the white light is applied to the body portion. In the special mode, the CPU 45 turns on the second light source 56, while turns off the first light source 55. Thus, only the narrow band light filtered through the wavelength tunable element 64 is applied to the body portion. Note that, in the case of a middle layer wavelength set, which is described later, both the first and second light sources 55 and 56 are used to apply the white light and the narrow band light in succession.

Figure 5:
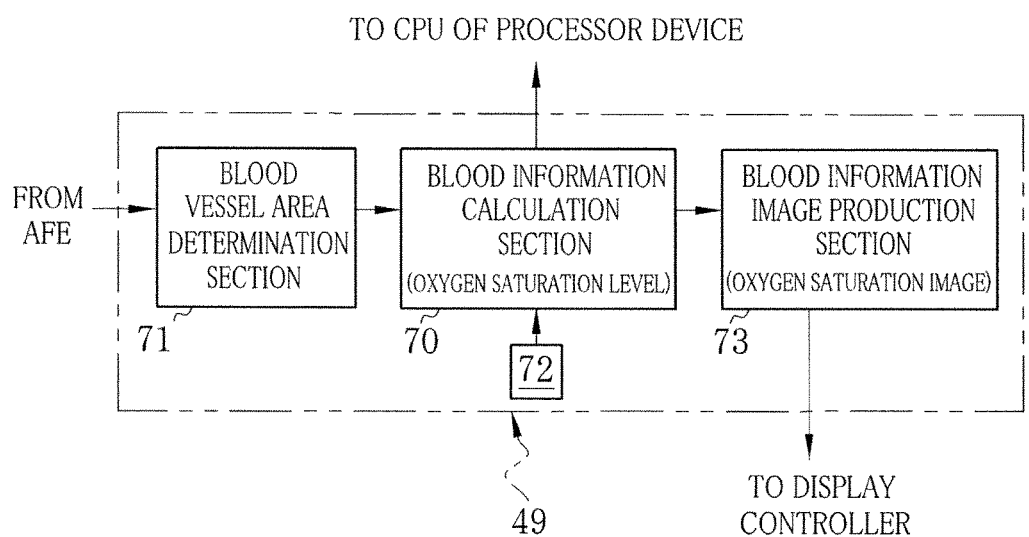
FIG. 5 is a block diagram of an image processor.

As shown in FIG. 5, the image processor 49 has a blood vessel area determination section 71, a blood information calculation section (oxygen saturation level calculation section) 70, and a blood information image production section (oxygen saturation image production section) 73. The blood vessel area determination section 71 analyzes the image inputted from the AFE 37, and determines (extracts) an area of a blood vessel in the image by referring to difference in a luminance value between the blood vessel area and the other area, for example. The blood information calculation section 70 calculates the blood information from the image signal of the determined blood vessel area. The blood information includes an oxygen saturation level of hemoglobin, a blood flow rate, the depth of the blood vessel, the density of the blood vessels, a blood flow speed, and the like. In this embodiment, measurement of the oxygen saturation level is described. Note that, the blood information may be calculated on the entire image, without determination of the blood vessel area.

Figure 6:
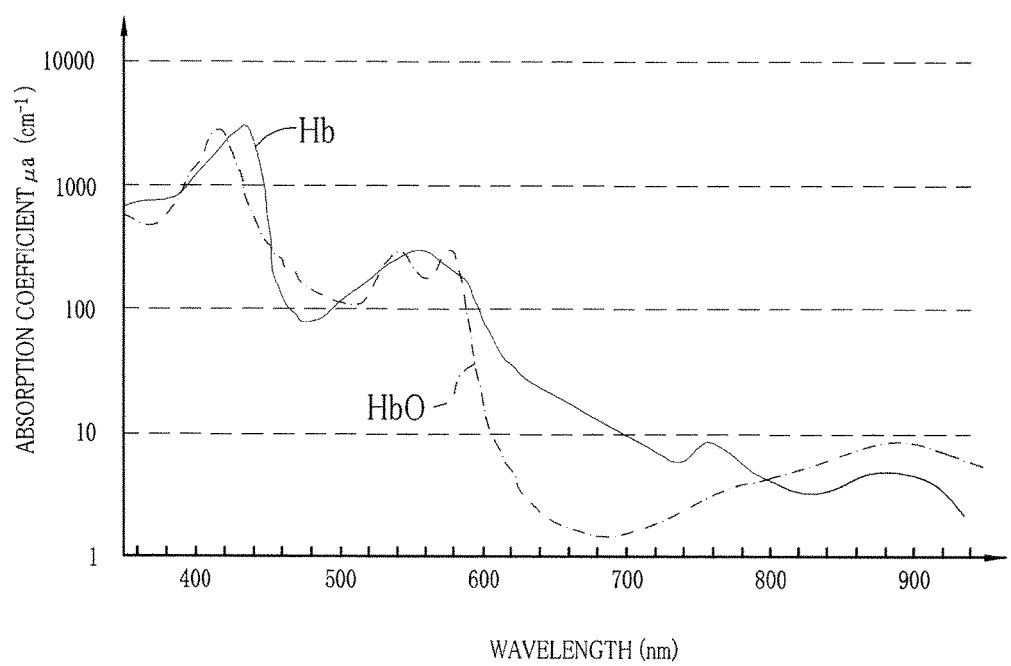
FIG. 6 is a graph showing absorption spectra of oxygenated hemoglobin and deoxygenated hemoglobin.

As shown in FIG. 6, an absorption coefficient $\mu a$ of hemoglobin varies with a wavelength of the illumination light. The absorption coefficient $\mu a$ represents the magnitude (absorbance) of light absorbed by the hemoglobin, and is a coefficient of an expression of $I_0 \exp(-\mu a \times x)$, which represents attenuation of light applied to the hemoglobin. Note that, $I_0$ denotes the intensity of the illumination light, and x (cm) denotes the depth to the blood vessel from a surface of the body portion.

An absorption spectrum of deoxygenated hemoglobin Hb not being bonded to oxygen is different from that of oxygenated hemoglobin HbO being bonded to oxygen. The deoxygenated hemoglobin Hb and the oxygenated hemoglobin HbO have the different absorption coefficients µa except at isosbestic points (intersection points of the absorption spectra of Hb and HbO) at which the deoxygenated hemoglobin Hb and the oxygenated hemoglobin HbO have the same absorption coefficient µa.

The difference in the absorption coefficient µa causes variation in the intensity of the reflected light, even if light of the same intensity and the same wavelength is applied to the same blood vessel. If light of the same intensity and different wavelengths is applied, the intensity of the reflected light is varied, because the absorption coefficient µa depends on the wavelength. For this reason, since the pickup signal varies based on the difference in the absorption coefficient µa, analyzing a plurality of images that are captured under a plurality of types of narrow band light of different wavelength bands makes it possible to obtain a ratio between the oxygenated hemoglobin and the deoxygenated hemoglobin in the blood vessel, that is, information of the oxygen saturation level.

The blood information calculation section 70 has a frame memory (not shown) that temporarily stores the plurality of images captured under the plurality of types of narrow band light of different wavelength bands. The blood information calculation section 70 reads out each image from the frame memory, and calculates image parameters by various arithmetic operations using the image signal of the blood vessel area determined in each image by the blood vessel area determination section 71, for example, from a ratio or difference in the image signal (pixel value) of the same color between frames. As for the blood vessel in a superficial layer, for example, blue narrow band light having a wavelength of 445 nm is applied to the body portion as first narrow band light being measurement light of the oxygen saturation level, and after that blue narrow band light having a wavelength of 405 nm is applied as second narrow band light being reference light, to obtain first and second images G1 and G2, respectively. The blood information calculation section 70 calculates G1/G2 as the image parameter for use in the calculation of the oxygen saturation level.

Figure 7:
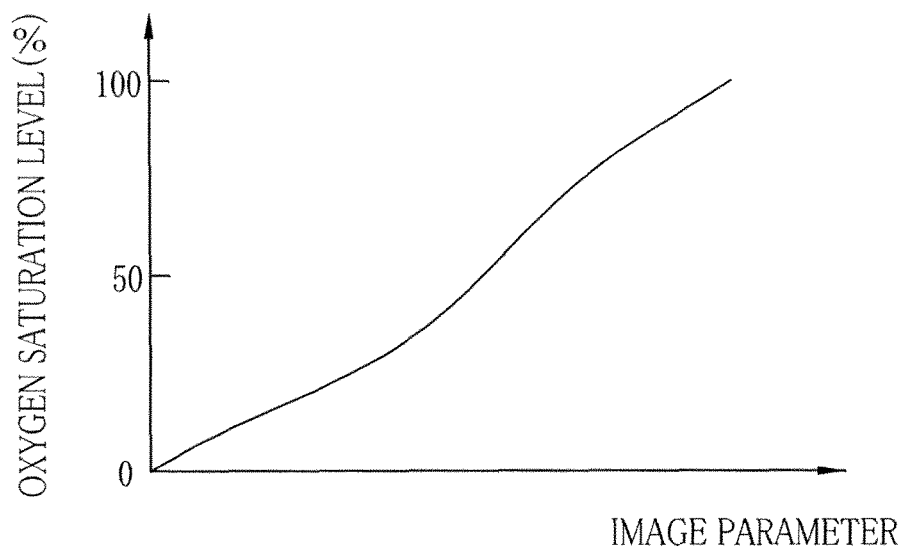
FIG. 7 is a graph showing an example of reference data.

Reference data 72 includes a function or a data table representing the relation between the image parameter and the oxygen saturation level, as shown in FIG. 7, on a wavelength set basis. The relation between the image parameter and the oxygen saturation level is obtained in advance by experiment and the like. The blood information calculation section 70 obtains the oxygen saturation level corresponding to the image parameter from the reference data 72 by substitution of the calculated image parameter into the function or a lookup on the data table. Then, a calculation result of the oxygen saturation level is outputted to the blood information image production section 73 and the CPU 45. Note that, the absorbance calculated from the image signals may be used as the image parameter.

The blood information image production section 73 produces an oxygen saturation image in which the calculation result is reflected based on a color map for displaying the calculation result of the blood information calculation section 70 with artificial colors. According to the color map, for example, cyan is assigned to a hypoxic region having the relative low oxygen saturation level. Magenta is assigned to a region having the middle oxygen saturation level, and yellow is assigned to a hyperoxic region having the relatively high oxygen saturation level. In addition, the oxygen saturation image may have text data representing a value of the oxygen saturation level, which the blood information calculation section 70 has calculated from the reference data 72.

Figure 8:
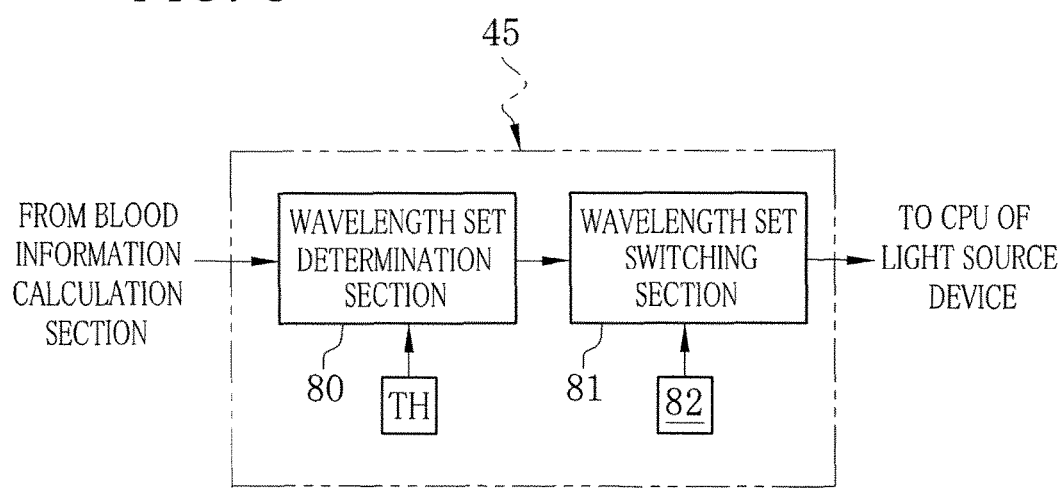
FIG. 8 is a block diagram showing structure of a CPU of a processor device.

As shown in FIG. 8, running the programs stored in the ROM 46 makes the CPU 45 function as a wavelength set determination section 80 and a wavelength set switching section 81. In the preliminary imaging operation described later in detail, the wavelength set determination section 80 compares the calculation result of the oxygen saturation level from the blood information calculation section 70 with a threshold value TH stored in advance on the ROM 46. The threshold value TH is set at a value of the oxygen saturation level that typical cancer tissue indicates, and is determined from examination data accumulated in past. When the calculation result of the oxygen saturation level is the threshold value TH or more, the wavelength set determination section 80 judges that no cancer tissue exists, and hence no additional examination (measurement) is performed. On the other hand, when the calculation result of the oxygen saturation level is less than the threshold value TH, the wavelength set determination section 80 judges that cancer tissue exists. In this case, the wavelength set determination section 80 outputs a hypoxic region detection signal, which indicates the existence of the cancer tissue, to the wavelength set switching section 81, and continues an additional examination of the cancer tissue. The unnecessity or continuation of the additional examination is displayed on the monitor 18.

Figures 9, 10:
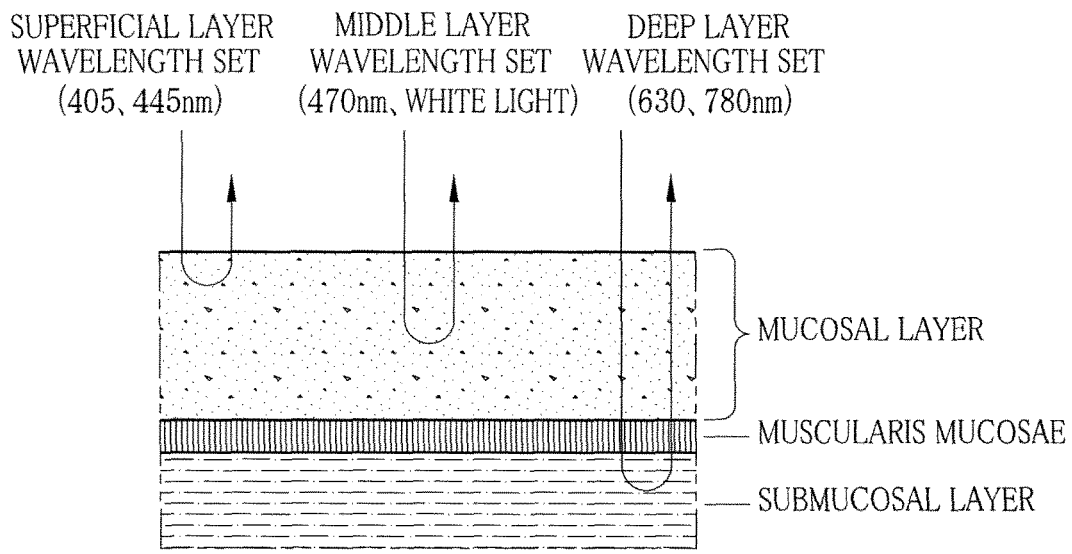
FIG. 9 is an example of a wavelength set table.
FIG. 10 is an explanatory view showing the penetration depth of each wavelength set.

The wavelength set switching section 81 chooses one of wavelength sets from a wavelength set table 82 of FIG. 9 stored on the ROM 46. Each wavelength set includes wavelengths of light used in calculation of the oxygen saturation level. In the wavelength set table 82, wavelength sets that are suited for calculation of the oxygen saturation level of the blood vessel at each of superficial, middle, and deep layers are stored in advance. Each wavelength set is chosen from the wavelengths that adequately penetrate into a target depth. Each wavelength set includes light (measurement light) in a wavelength band at which the absorption coefficient µa of the oxygenated hemoglobin much differs from that of the deoxygenated hemoglobin, and light (reference light) in a wavelength band of the isosbestic point without having the difference in the absorption coefficient µa. By way of example, a superficial layer wavelength set includes narrow band light (reference light) of 405 nm and narrow band light (measurement light) of 445 nm chosen from a relatively short wavelength band. A deep layer wavelength set includes narrow band light (measurement light) of 630 nm and narrow band light (reference light) of 780 nm chosen from a long wavelength band including near infrared light. A middle layer wavelength set includes white light (reference light) and narrow band light (measurement light) of 473 nm chosen from a green wavelength band intermediate between the short and long wavelength bands.

As shown in FIG. 10, the superficial layer wavelength set reaches a depth of the order of several tens of micrometers from the surface of a mucosal layer. The middle layer wavelength set reaches a depth of several tens to several hundreds of micrometers, which is deeper than the depth the superficial layer wavelength set reaches. The deep layer wavelength set reaches a depth from a muscularis mucosae to a submucosal layer. Note that, each wavelength set has the two wavelengths in this embodiment, but may have three or more wavelengths. For example, as described in US Patent Application Publication No. 2011/0077462, if each wavelength set may have three wavelengths, it is possible to eliminate an effect of depth on the oxygen saturation level, and calculate the oxygen saturation level more accurately.

Figure 11:
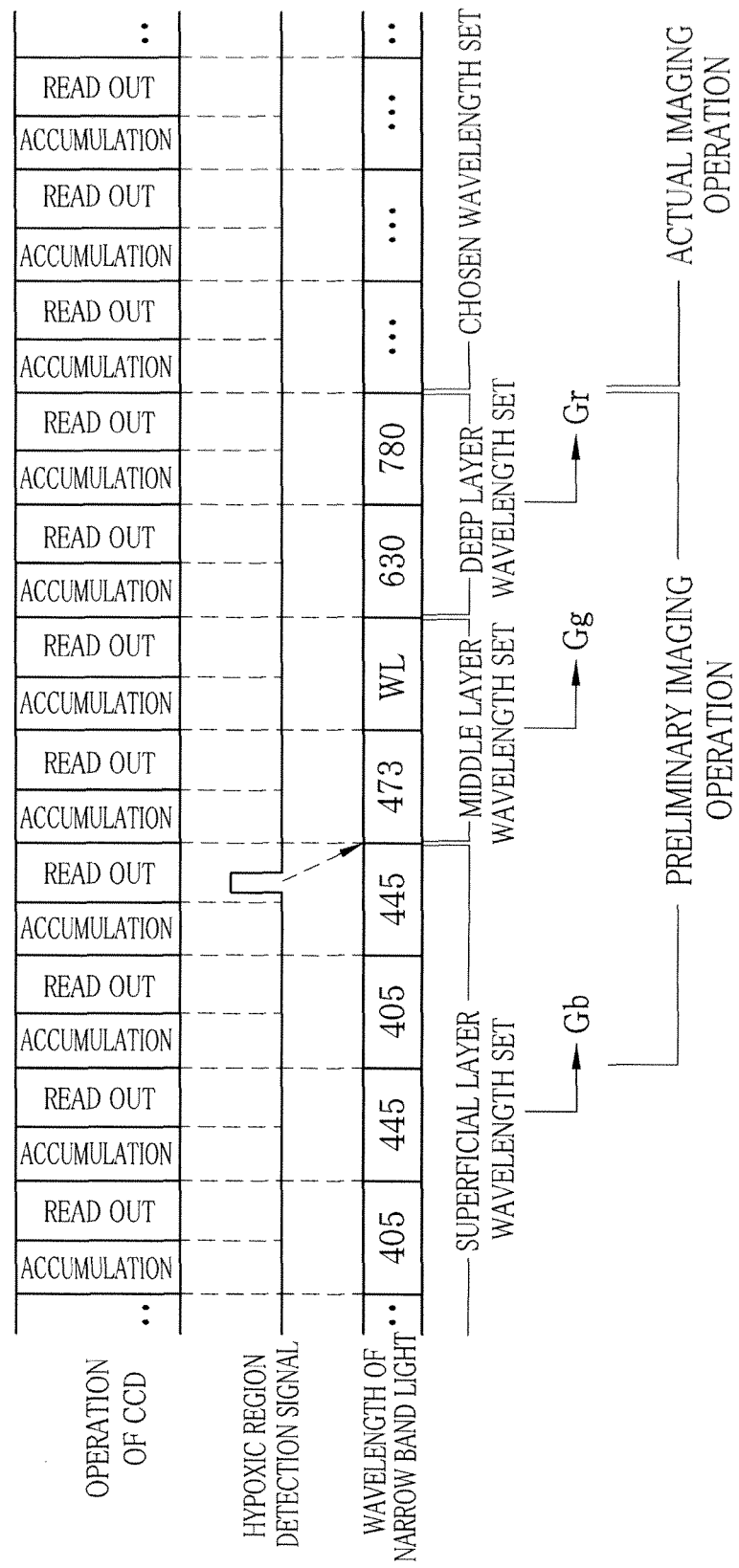
FIG. 11 is a timing chart of switching among the wavelength sets.

As shown in FIG. 11, when the blood information measuring apparatus 2 is put into the special mode by operation of the mode switch 19, the wavelength set switching section 81 chooses the superficial layer wavelength set as an abnormality detection wavelength set for detecting the hypoxic region (abnormal region). The CPU 66 of the light source device 12 controls operation of the wavelength tunable element 64 such that the two types of narrow band light of the superficial layer wavelength set are successively emitted in synchronization with a charge accumulation period of the CCD 33. Upon input of the hypoxic region detection signal from the wavelength set determination section 80, the wavelength set switching section 81 outputs to the CPU 66 signals that indicate switching from the superficial layer wavelength set to the middle layer wavelength set and switching from the middle layer wavelength set to the deep layer wavelength set. Thus, the CPU 66 controls the operation of the wavelength tunable element 64 so as to successively emit the narrow band light and the white light of the middle layer wavelength set and thereafter the narrow band light of the deep layer wavelength set in synchronization with the charge accumulation period of the CCD 33. The switching order of the middle layer wavelength set and the deep layer wavelength set is permutable. Hereafter, the preliminary imaging operation refers to the above operation sequence in which the images are captured while the wavelength sets are switched among the superficial layer wavelength set, the middle layer wavelength set, and the deep layer wavelength set upon output of the hypoxic region detection signal. The actual imaging operation refers to operation in which the images are captured under the light of the wavelength set that is determined after the preliminary imaging operation.

An oxygen saturation image Gb is obtained under the light of the superficial layer wavelength set, and triggers the output of the hypoxic region detection signal. An oxygen saturation image Gg is obtained under the light of the middle layer wavelength set. An oxygen saturation image Gr is obtained under the light of the deep layer wavelength set. These oxygen saturation images Gb, Gg, and Gr indicate information of the oxygen saturation level of the body portion, which the wavelength set determination section 80 judges to be the hypoxic region, with respect to a depth direction.

As is widely known, cancer tissue induces blood vessel growth (angiogenesis) by secreting various growth factors such as a vascular endothelial growth factor (VEGF), being a major contributor to angiogenesis. The VEGF can induce capillary growth (neovascularization) and increase a blood flow into the cancer tissue, to make up for a lack of oxygen and other essential nutrients required for the spread or metastasis of the cancer tissue. A neovascular network including newly-formed capillaries grows inward from the cancer tissue and is connected to a thick blood vessel in the submucosal layer. Thus, the cancer tissue itself has the relatively low oxygen saturation level (hypoxic region), while a region of the newly-formed capillaries surrounding the cancer tissue has the relatively high oxygen saturation level (hyperoxic region).

Figure 12A:
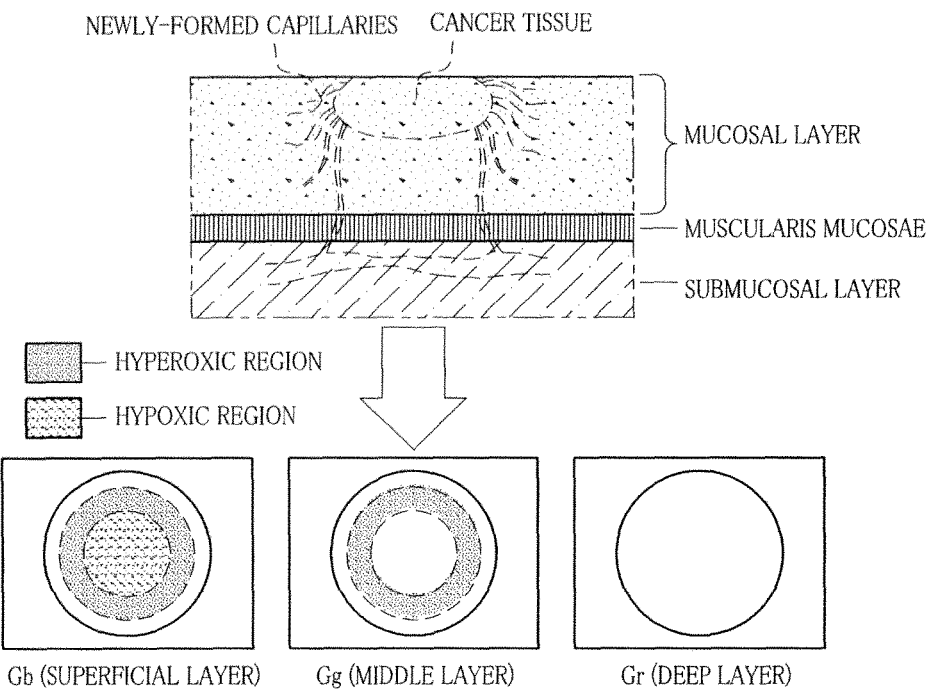
FIG. 12A is an explanatory view showing an example of oxygen saturation images of early stage cancer captured under light of each wavelength set.

As shown in FIG. 12A, in the case of early stage cancer the tissue of which is present within the mucosal layer and does not invade the muscularis mucosae, the newly-formed capillaries surround the cancer tissue from the surface to the middle of the mucosal layer. The oxygen saturation image Gb of the cancer tissue and its surroundings represents a hypoxic central region corresponding to the cancer tissue and a hyperoxic annular region corresponding to the newly-formed capillaries, in general. The oxygen saturation image Gg under the light of the middle layer wavelength set represents no region corresponding to the cancer tissue, while represents only a hyperoxic annular region corresponding to the newly-formed capillaries. The oxygen saturation image Gr under the light of the deep layer wavelength set represents no variation of the oxygen saturation level.

Figure 12B:
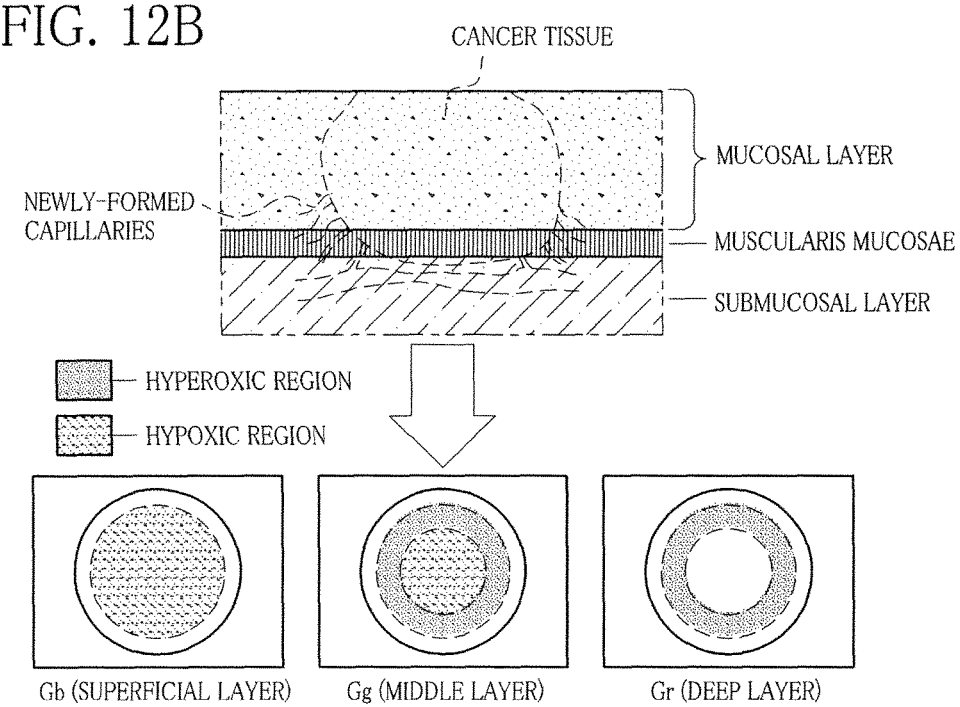
FIG. 12B is an explanatory view showing an example of oxygen saturation images of advanced stage cancer captured under the light of each wavelength set.

On the other hand, in the case of advanced stage cancer the tissue of which is spread from the mucosal layer to the submucosal layer, as shown in FIG. 12B, the oxygen saturation image Gb is almost occupied with a hypoxic region corresponding to the cancer tissue. The oxygen saturation image Gg represents a hypoxic central region corresponding to the cancer tissue and a hyperoxic annular region corresponding to the newly-formed capillaries, just as with the oxygen saturation image Gb of FIG. 12A. The oxygen saturation image Gr represents only a hyperoxic annular region corresponding to the newly-formed capillaries.

Figure 15:
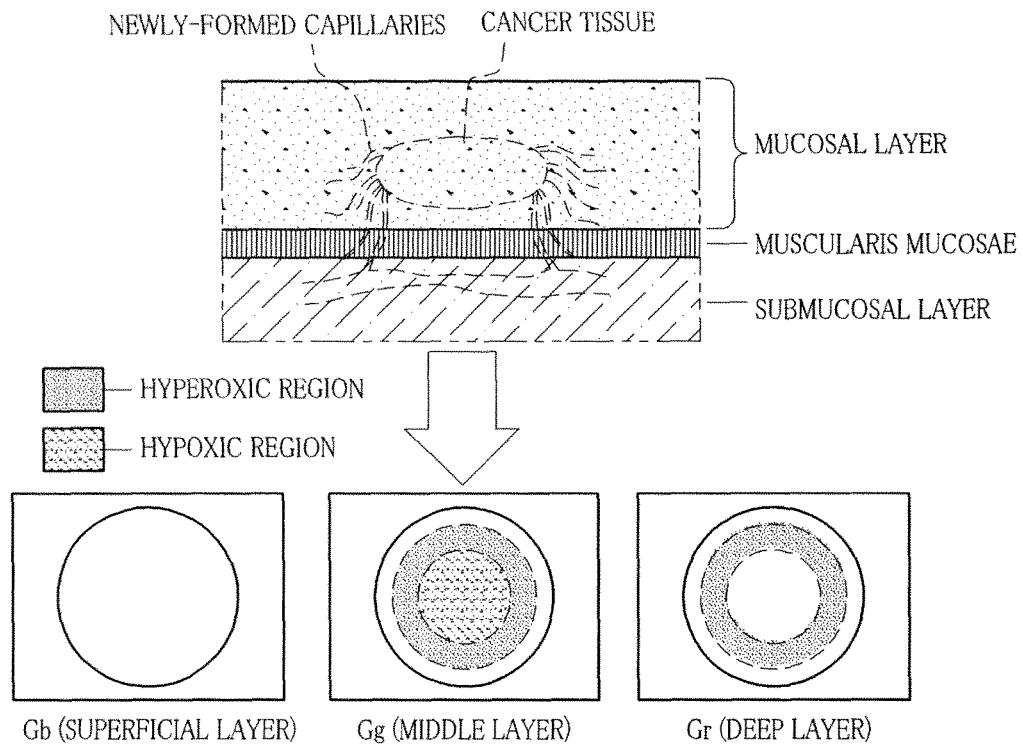
FIG. 15 is an explanatory view showing an example of oxygen saturation images of cancer covered with normal appearing mucosa captured under the light of each wavelength set.

As described above, the distribution of the hypoxic and hyperoxic regions seen in the oxygen saturation images Gb, Gg, and Gr depends on the stage of the cancer. Additionally, as shown in FIG. 15, some types of cancer do not manifest themselves in the surface of the mucosal layer, but occur from the middle to the depths of the mucosal layer. For this reason, the wavelength set suitable for diagnosis differs from lesion to lesion in accordance with the stage and type of the cancer. Therefore, by analyzing a pattern of the hypoxic and hyperoxic regions in the oxygen saturation images Gb, Gg, and Gr obtained in the preliminary imaging operation, the wavelength set suitable for the actual imaging operation is determined as follows.

First, the blood information calculation section 70 outputs to the wavelength set determination section 80 calculation results of the oxygen saturation level of the oxygen saturation images Gb, Gg, and Gr obtained in the preliminary imaging operation. The wavelength set determination section 80 grades a value of the oxygen saturation level of each pixel (from 0 to 10%, from 11 to 20%, and the like), to create three histograms of the oxygen saturation images Gb, Gg, and Gr, respectively, using the frequency of occurrence of each grade.

Figure 13A:
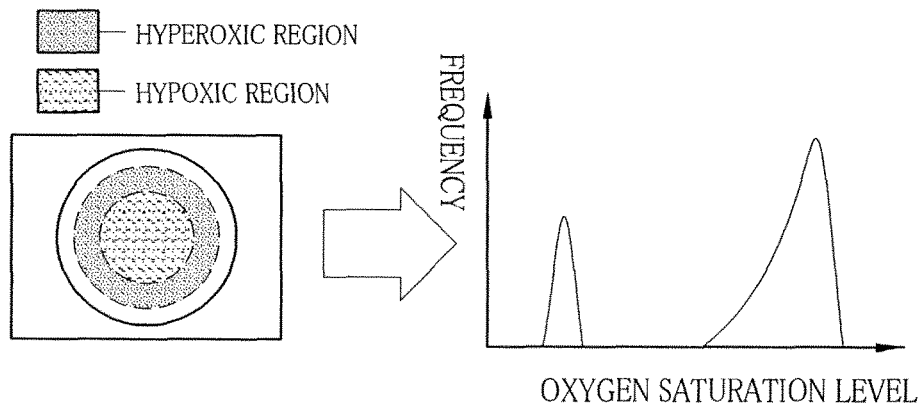
FIGS. 13A to 13D are explanatory views showing histograms of the typical oxygen saturation images.
Figure 13B:
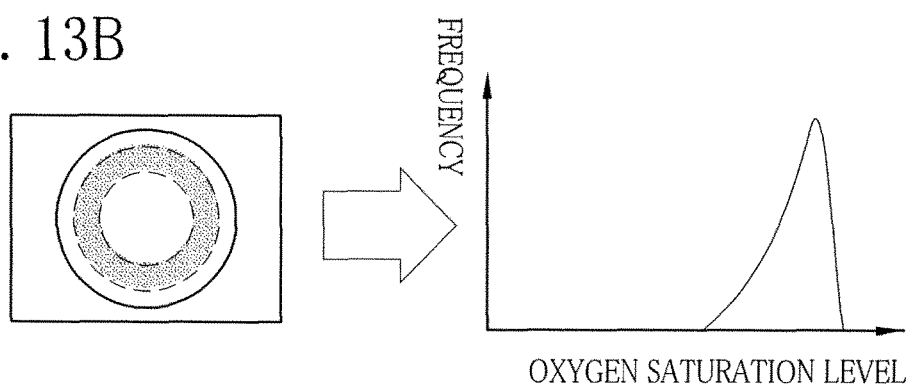
Figure 13C:
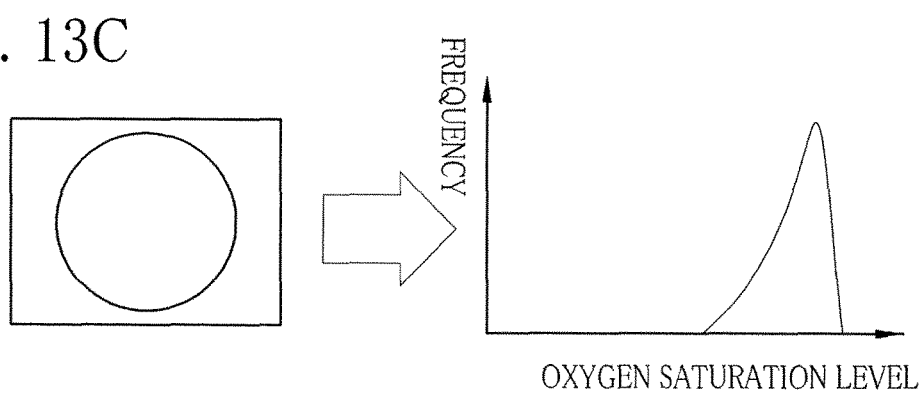
Figure 13D:
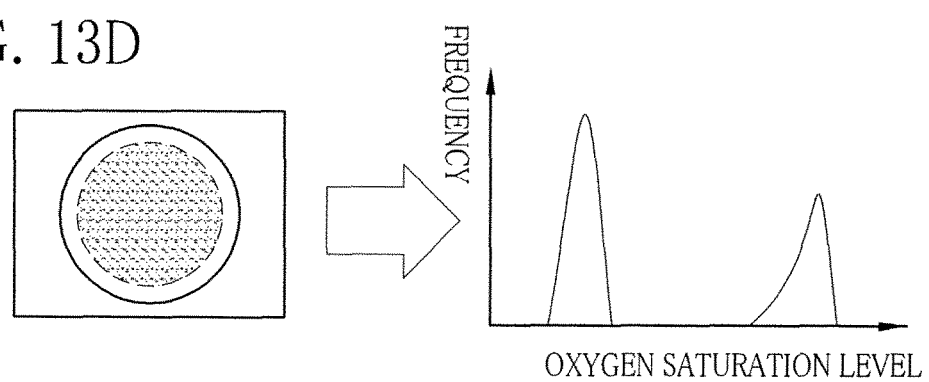

FIGS. 13A to 13D represent histograms of the typical oxygen saturation images seen in FIGS. 12A and 12B. As shown in FIG. 13A, in the oxygen saturation image Gb of the early stage cancer or the oxygen saturation image Gg of the advanced stage cancer, the hyperoxic region and the hypoxic region are mixed. Thus, its histogram represents two frequency peaks, one at a high oxygen saturation level and one at a low oxygen saturation level. In the case of the oxygen saturation image Gg of the early stage cancer or the oxygen saturation image Gr of the advanced stage cancer, as shown in FIG. 13B, the histogram represents a frequency peak at the high oxygen saturation level. Likewise, in the case of the oxygen saturation image Gr of the early stage cancer, as shown in FIG. 13C, the histogram represents a frequency peak at the high oxygen saturation level. In the case of the oxygen saturation image Gb of the advanced stage cancer, as shown in FIG. 13D, the histogram represents two frequency peaks, large one at the low oxygen saturation level and small one at the high oxygen saturation level.

The wavelength set determination section 80 calculates a variance $\sigma^2$ of each of the three histograms corresponding to the oxygen saturation images Gb, Gg, and Gr, respectively. As is widely known, the variance $\sigma^2$ calculated by $\sigma^2 = \Sigma(X-X')^2/n$, in which summation of the squares of the difference of a frequency X of each grade from a frequency mean X' is divided by the number n of the grades, is an index of bias (alienation from a mean) of the frequency of the histogram. In the cases of the FIGS. 13B and 13C in which the frequency peak is present only at the high oxygen saturation level, the variance $\sigma^2$ becomes small. On the other hand, in the cases of the FIGS. 13A and 13D in which the hyperoxic region and the hypoxic region are mixed, the variance $\sigma^2$ becomes large. Note that, a standard deviation a being the square root of the variance $\sigma^2$ may be used instead of the variance $\sigma^2$.

The wavelength set determination section 80 notifies the wavelength set switching section 81 which one of the oxygen saturation images Gb, Gg, and Gr has the histogram with the maximum variance $\sigma^2$, based on the variances $\sigma^2$ of the oxygen saturation images Gb, Gg, and Gr. Based on information inputted from the wavelength set determination section 80, the wavelength set switching section 81 chooses the wavelength set (actual imaging wavelength set) to be used in the actual imaging operation. More specifically, the larger the variance $\sigma^2$, the more likely the hyperoxic region and the hypoxic region are mixed, and the clearer the difference between the hyperoxic region and the hypoxic region is. For this reason, the wavelength set corresponding to the histogram having the maximum variance $\sigma^2$ is chosen as the actual imaging wavelength set. For example, in the case of the early stage cancer of FIG. 12A, the superficial layer wavelength set is chosen as the actual imaging wavelength set. In the case of the advanced stage cancer of FIG. 12B, the superficial or middle layer wavelength set is chosen as the actual imaging wavelength set.

After the determination of the actual imaging wavelength set, the wavelength set switching section 81 issues a switching signal to the CPU 66. The CPU 66 controls the operation of the wavelength tunable element 64, such that the two types of light of the actual imaging wavelength set are successively emitted in synchronization with the charge accumulation period of the CCD 33. This actual imaging operation is continued until the doctor commands completion from the operation unit 48 or the like.

Figure 14:
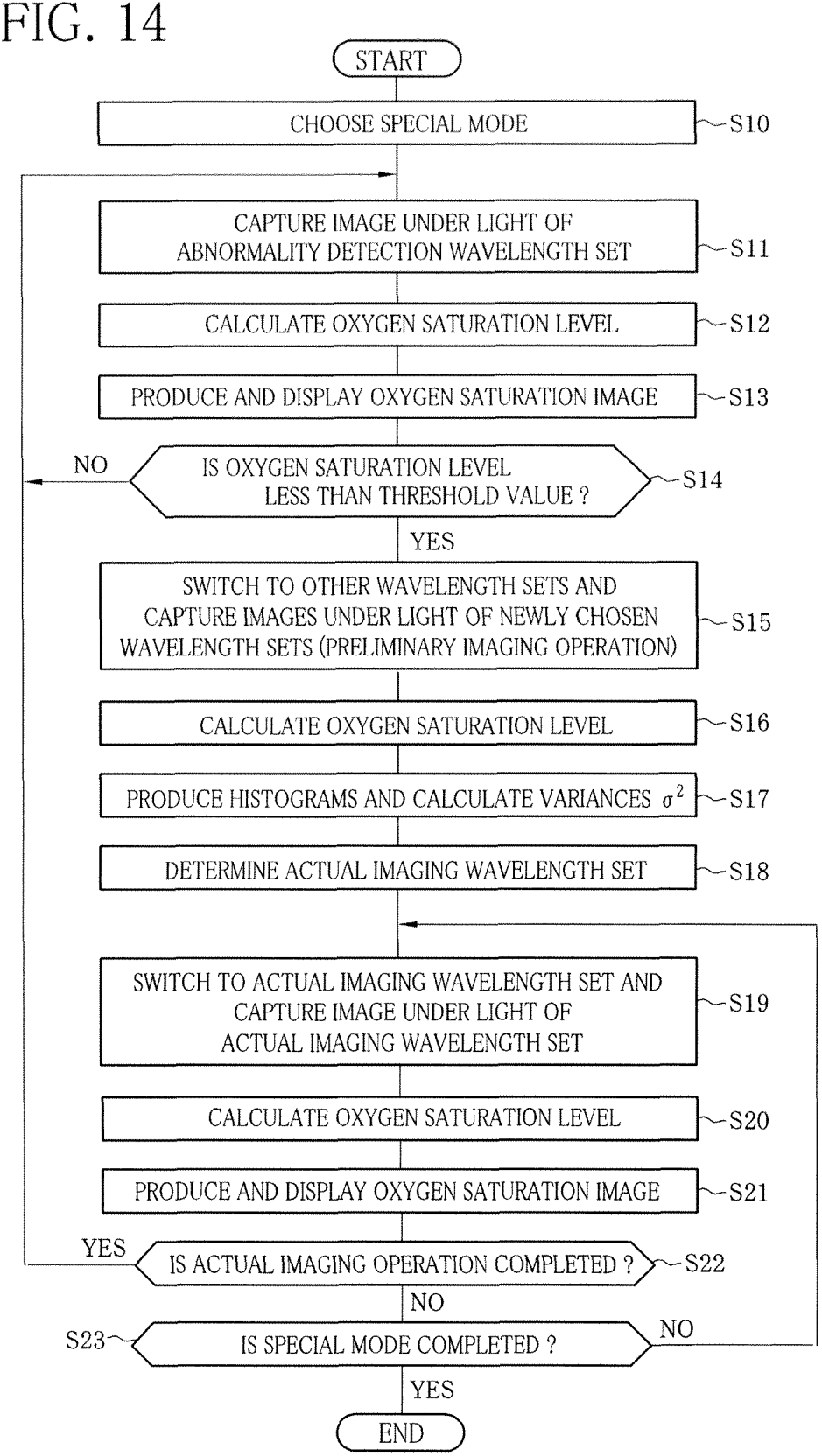
FIG. 14 is a flowchart of an operation process in a special mode.

Next, the operation of the above embodiment will be described with referring to FIG. 14. In observing the inside of the patient's body with the electronic endoscope 10, the doctor inputs the patient information and the like and commands the start of an examination from the operation unit 48. After the start of the examination, the insert section 13 of the electronic endoscope 10 is introduced into the patient's body cavity. While the inside of the patient's body is irradiated with the illumination light from the light source device 12, the COD 33 captures an image of the inside of the body. The obtained image is displayed on the monitor 18.

To be more specific, an image signal outputted from the CCD 33 is subjected to various processes in each component of the AFE 37, and is inputted to the image processor 49. The image processor 49 applies the various image processes to the inputted image signal, and produces the image of the inside of the body. The image processed by the image processor 49 is inputted to the display controller 50. The display controller 50 performs the various display control processes in accordance with the graphic data. Thereby, the observation image is displayed on the monitor 18.

During the observation of the inside of the body, an observation mode is switched as necessary. When the insert section 13 of the electronic endoscope 10 is introduced into the patient's body cavity, the normal mode is chosen, so the doctor carries out insertion operation with a wide view while looking at the image of the inside of the body captured under the white light. When a lesion that needs detail inspection is found out and the oxygen saturation level of the lesion is obtained, the special mode is chosen to obtain the oxygen saturation images captured under the light of the appropriate wavelength set. As necessary, the still image is captured by operating the release button provided on the electronic endoscope 10. If some treatment is required, a necessary medical instrument is inserted into the channel of the electronic endoscope 10 to perform removal of the lesion, administration of a drug, and the like.

In the normal mode, the CPU 45 commands the CPU 66 to turn on the first light source 55, so the white light is applied from the lighting window 31 to the body portion.

On the other hand, when the special mode is chosen by operation of the mode switch 19, as shown in S10, the wavelength set switching section 81 chooses the superficial layer wavelength set as the abnormality detection wavelength set. The CPU 66 turns off the first light source 55, and turns on the second light source 56. The CCD 33 captures the observation image (S11), while the two types of narrow band light having wavelengths of 405 nm and 445 nm of the abnormality detection wavelength set are successively emitted in synchronization with the charge accumulation period of the CCD 33 by control of the wavelength tunable element 64.

In the image processor 49, the blood vessel area determination section 71 determines the blood vessel area, and then the blood information calculation section 70 calculates the oxygen saturation level of hemoglobin in the blood vessel based on the reference data 72 (S12). The blood information image production section 73 produces the oxygen saturation image Gb based on the calculation result of the oxygen saturation level. The oxygen saturation image Gb is displayed on the monitor 18 (S13).

The calculation result of the oxygen saturation level is outputted to the CPU 45 of the processor device 11. In the CPU 45, the wavelength set determination section 80 compares the calculation result of the oxygen saturation level with the threshold value TH (S14).

If the calculation result of the oxygen saturation level is equal to or more than the threshold value TH (NO in S14), the wavelength set is not changed. The capture of the image under the narrow band light of the superficial layer wavelength set (S11), the calculation of the oxygen saturation level (S12), and the production and display of the oxygen saturation image Gb (S13) are repeated. On the other hand, if the calculation result of the oxygen saturation level is less than the threshold value TH (YES in S14), the wavelength set determination section 80 issues the hypoxic region detection signal to the wavelength set switching section 81.

In response to input of the hypoxic region detection signal from the wavelength set determination section 80, the wavelength set switching section 81 outputs to the CPU 66 the signal that indicates the successive switching to the middle layer wavelength set and the deep layer wavelength set. By control of the CPU 66, the wavelength tunable element 64 extracts light of a desired wavelength band out of the white light of the second light source 56, so that the narrow band light (473 nm) and the white light (turn on the first light source 55) of the middle layer wavelength set and narrow band light (630 nm and 780 nm) of the deep layer wavelength set are successively emitted in synchronization with the charge accumulation period of the CCD 33. The CCD 33 captures the images of the body portion under the middle layer wavelength set and the deep layer wavelength set (S15).

The blood information calculation section 70 calculates the oxygen saturation level based on the image data captured under the middle layer wavelength set and the deep layer wavelength set (S16). The wavelength set determination section 80 creates the three histograms of the oxygen saturation images Gb, Gg, and Gr obtained with the superficial, middle, and deep layer wavelength sets, respectively, based on the calculation results of the oxygen saturation level. Subsequently, the wavelength set determination section 80 calculates the variance $\sigma^2$ of each histogram (S17).

Based on the calculated three variances $\sigma^2$, the wavelength set determination section 80 chooses the wavelength set corresponding to the histogram having the maximum variance $\sigma^2$ as the actual imaging wavelength set (S18). After that, the wavelength switching section 81 outputs to the CPU 66 the signal for commanding emission of the light of the actual imaging wavelength set. The CPU 66 controls the operation of the wavelength tunable element 64, so as to successively emit the light of the actual imaging wavelength set in synchronization with the charge accumulation period of the CCD 33 (S19).

Just as with S12, the CCD 33 captures the images of the body portion under the light of the actual imaging wavelength set. The blood information calculation section 70 calculates the oxygen saturation level based on the obtained image data (S20). Then, the oxygen saturation image is produced by the blood information image production section 73, and displayed on the monitor 18 (S21). When the doctor commands completion of the actual imaging operation from the operation unit 48 or the like (YES in S22), the process returns to S11, so the light of the superficial layer wavelength set as the abnormality detection wavelength set is emitted again. The above process is continued, until the special mode is ended (YES in S23).

As described above, in the preliminary imaging operation in which the images are captured while switching the wavelength sets, the oxygen saturation level of each wavelength set is calculated. Based on the preliminary imaging operation, the wavelength set to be used in the actual imaging operation is determined. This allows efficient obtainment of the oxygen saturation level of the lesion with the wavelength set suitable for diagnosis, while saving time and trouble for the doctor.

Note that, to determine the actual imaging wavelength set, a method other than the method using the variances $\sigma^2$ of the histograms is available. For example, a value (S1−S2)/S' in which the difference of an average oxygen saturation level S1 of the blood vessel area extracted by the blood vessel area determination section 71 and an average oxygen saturation level S2 of the other area (mucosal layer) is divided by a mean value S' of the oxygen saturation level of the entire image may be used as an index for choosing the actual imaging wavelength set. In this case, just as in the case of using the variances $\sigma^2$, the wavelength set that corresponds to the maximum value of (S1−S2)/S' is chosen as the actual imaging wavelength set.

In another case, out of three means values S' of the oxygen saturation level, the wavelength set that corresponds to the minimum mean value S' may be chosen as the actual imaging wavelength set. In further another case, the actual imaging wavelength set may be determined in accordance with the density of the blood vessels extracted by the blood vessel area determination section 71, instead of using the oxygen saturation level. The density of the blood vessels is obtained by image analysis e.g. by analyzing how many branches the single blood vessel is divided into. Since the newly-formed capillaries related to the cancer tissue have the relatively high density of the blood vessels, the wavelength set that corresponds to the image having the density higher than a threshold value may be chosen as the actual imaging wavelength set.

When producing the oxygen saturation images Gb, Gg, and Gr in the preliminary imaging operation, the image processor 49 may perform a binning process. In the binning process, a pixel value of a plurality of adjoining pixels (for example, four pixels of two-by-two pixels) is added to assume a sum as a signal of one pixel. The binning process significantly reduces the size of the picture signal to be dealt with in later processes, and increases process speed. Also, the apparent sensitivity (S/N ratio) of the COD 33 is increased because the plurality of pixels are assumed as the single pixel. On the other hand, the resolution of the CCD 33 is reduced. However, the reduction of the resolution hardly affects the diagnosis, because oxygen saturation images Gb, Gg, and Gr obtained in the preliminary imaging operation are not displayed on the monitor 18 but used only for determination of the actual imaging wavelength set. To further increase the process speed, the oxygen saturation images Gb, Gg, and Gr may be read out with pixel skipping.

As a matter of course, the histograms created by the wavelength set determination section 80 may be displayed on the monitor 18 together with the oxygen saturation images Gb, Gg, and Gr obtained in the preliminary imaging operation. The oxygen saturation images Gb, Gg, and Gr and their histograms and variances $\sigma^2$ may be stored to an external memory such as a removable medium with relation to each other.

At present, in a field of observation of the cancer tissue with the narrow band light, a diagnostic method using an image of capillaries in the superficial layer has been established, and there is an interest in the oxygen saturation level of the capillaries in the superficial layer. For this reason, in this embodiment, the superficial layer wavelength set is chosen as the abnormality detection wavelength set for detecting the hypoxic region. In a case where the body portion to be observed is located in the esophagus or the large intestine, the superficial layer wavelength set is preferably chosen as the abnormality detection wavelength set.

The abnormality detection wavelength set is not limited to the superficial layer wavelength set, but the middle layer wavelength set may be chosen instead. The superficial layer wavelength set can detect the hypoxic region (cancer tissue) present in the surface of the mucosal layer, but is not suited for finding out scirrhous carcinoma in which a surface of a lesion is covered with normal tissue or normal tissue is left in the lesion in a discrete manner. It is also known that the scirrhous carcinoma thickens the mucosal layer of a stomach wall. To find out the scirrhous carcinoma, which does not have the hypoxic region in the surface of the mucosal layer, the middle layer wavelength set is preferably chosen as the abnormality detection wavelength set, because the middle layer wavelength set is suited for calculation of the oxygen saturation level of hemoglobin in a relatively thick blood vessel in the middle of mucosal layer.

Figure 16:
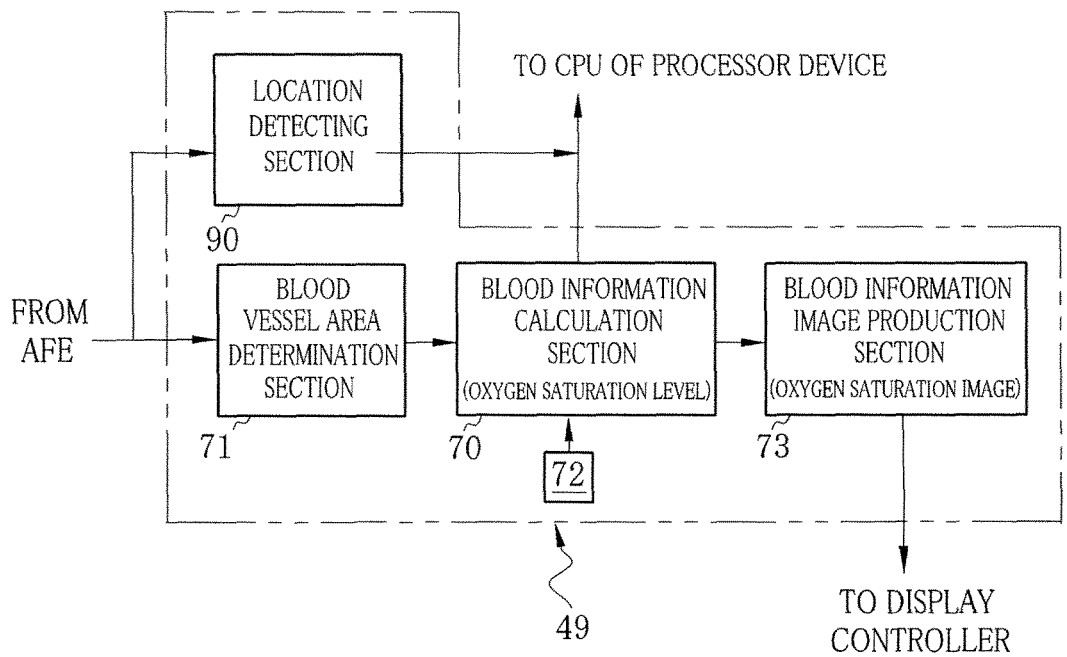
FIG. 16 is a block diagram of an image processor according to a second embodiment.

The abnormality detection wavelength set may be switched in accordance with the body portion to be examined, instead of being fixed at the specific wavelength set. For example, in a case where the electronic endoscope 10 is an esophagogastro-duodenoscope, the superficial layer wavelength set is chosen as the abnormality detection wavelength set when observing esophagus, and the middle layer wavelength set is chosen as the abnormality detection wavelength set when observing stomach to facilitate finding out the scirrhous carcinoma. The abnormality detection wavelength set may be switched manually by operating a specific button or knob provided on the handling section 14 or the like of the electronic endoscope 10. In another case, the image processor 49 may include a location detecting section 90, as shown in FIG. 16. The location detecting section 90 distinguishes whether the body portion to be examined is in the esophagus or the stomach by a well-known image recognition technique and the like. The abnormality detection wavelength set may be automatically switched in accordance with a distinction result.

The image recognition technique includes a method by which the location detecting section 90 recognizes a pattern of cardia, which has a unique shape, positioned in a juncture between the esophagus and the stomach. There is also a method by which the size of a dark section may be compared with a threshold value, because the size of the dark section seen in the image is small during a course from the esophagus to the cardia, while it is large in the stomach. Another method other than the image recognition technique may be available too. For example, the position of the distal end portion 17 of the electronic endoscope 10 may be detected by CT, or the distal end portion 17 may be provided with a pH sensor to take advantage of difference in pH between the esophagus and the stomach.

When the middle layer wavelength set is chosen as the abnormality detection wavelength set, the threshold value TH used in the wavelength set determination section 80 is changed to another value specific to the middle layer wavelength set. Furthermore, if the wavelength set determination section 80 has judged that the calculation result of the oxygen saturation level is less than the threshold value TH, the wavelength set switching section 81 switches from the middle layer wavelength set to the superficial layer wavelength set and then to the deep layer wavelength set. After the calculation of the oxygen saturation level with the deep layer wavelength set, the middle layer wavelength set is chosen again. Omitting the switching to the superficial layer wavelength set, the switching only to the deep layer wavelength set may be performed.

The wavelength set table 82 of FIG. 9 represents just an example of the wavelength sets. Another wavelength set being a combination of other wavelengths may be used in addition to or instead of the wavelength sets of the table 82. For example, the mucosal layer may be subdivided into surface, middle, and deep layers, and wavelength sets for the subdivided surface, middle, and deep layers may be prepared.

Instead of the hypoxic region, the hyperoxic region may be detected using the abnormality detection wavelength set, and the wavelength set may be switched in response to the detection of the hyperoxic region. The doctor visually detects the abnormal region through the image in the normal mode, instead of detecting the abnormal region in the image obtained under the narrow band light in the special mode. In the case of follow-up observation after a surgical operation, the abnormal region may be located from an image obtained another modality such as CT or MRI.

The special mode may include a mode of obtaining a blood vessel image (visible image of a blood vessel route) of each of the superficial, middle, and deep layers by applying one type of narrow band light of each layer, a mode of observing fluorescence emitted from the body portion by application of excitation light after administration of a fluorescent substance to living body tissue, a mode for observing autofluorescence of living body tissue, and the like.

The wavelength tunable element 64 may be disposed at an exit end of the light guide 34b, instead of between the second light source 56 and the light guide 34b. In another case, the wavelength tunable element may be disposed not in a lighting optical system but in an objective optical system for taking the image of the body portion, for example, behind the imaging window 30 or on the imaging plane of the CCD 33. Furthermore, instead of provision of the wavelength tunable element, a plurality of light sources (semiconductor lasers or the like) each for emitting narrow band light of a specific wavelength band may be provided.

The blood information to be obtained is not limited to the oxygen saturation level of hemoglobin. The blood information includes the blood flow rate (the sum of oxygenated hemoglobin and deoxygenated hemoglobin), an oxygenated hemoglobin index calculated by "blood flow rate×oxygen saturation level (%)", an deoxygenated hemoglobin index calculated by "blood flow rate×(100−oxygen saturation level) (%)", and the like. The blood information may be calculated at a minute spot, instead of at an imaging area of the CCD as described above.

The electronic endoscope is used in the above embodiment, but other types of endoscopes are available including a fiberscope with an image guide, an ultrasonic endoscope having an imaging device and an ultrasonic transducer at its distal end, and the like. The present invention is applicable to a system that obtains information of the oxygen saturation level and the like by applying the narrow band light to a surface of the patient's body, instead of the inside of the patient's body. In such a case, the insert section to be introduced into the patient's body is unnecessary.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A blood information measuring apparatus comprising:
a light source which applies illumination light to a body portion having a blood vessel;
an imaging device which performs photoelectric conversion of reflected light from said body portion irradiated with said illumination light and outputting an image signal;
a wavelength tunable element which narrows a wavelength band of said illumination light to be applied to said body portion or said reflected light to be incident on said imaging section; and
a processor, said processor configured for:
calculating oxygen saturation information based on said image signal;
driving said wavelength tunable element to switch among a superficial layer wavelength set having a plurality of types of narrow band light in a blue wavelength band, a middle layer wavelength set having a plurality of types of narrow band light in a green wavelength band and a deep layer wavelength set having a plurality of types of narrow band light in a red wavelength band;
performing preliminary imaging operation, in said preliminary imaging operation, a preliminary image of said body portion in each of said wavelength sets is captured while automatically switching among said superficial layer wavelength set, said middle layer wavelength set and said deep layer wavelength set;
automatically choosing one of said wavelength sets as an actual imaging wavelength set to be used in actual imaging operation by analyzing a pattern of hypoxic and hyperoxic regions of each of said preliminary images, said actual imaging set wavelength corresponding to said preliminary image in which a mixed degree of said hyperoxic region and said hypoxic region is highest among said preliminary images;

performing said actual imaging operation in which an actual image is captured with use of said actual imaging wavelength set; and displaying on a monitor said oxygen saturation information measured in said actual imaging operation, wherein the processor detects a location of said body portion in a body cavity, and chooses one of said superficial layer wavelength set, said middle layer wavelength set and said deep layer wavelength set as an abnormality detection wavelength set in accordance with said location, and wherein said processor starts said preliminary imaging operation if a mean value of said oxygen saturation level obtained with said abnormality detection wavelength set is less than a threshold value.

2. The blood information measuring apparatus according to claim 1, wherein said processor creates a histogram of said oxygen saturation level of each of said preliminary images independently from one of said wavelength sets to another, and determines said actual imaging wavelength set based on said histograms.

3. The blood information measuring apparatus according to claim 2, wherein one of said wavelength sets corresponding to said histogram having a maximum variance or a maximum standard deviation is chosen as said actual imaging wavelength set.

4. The blood information measuring apparatus according to claim 1, wherein said processor determines a blood vessel area from said image signal, calculates a difference between a mean value of said oxygen saturation level of said blood vessel area and that of another area independently from one of said wavelength sets to another, and chooses one of said wavelength sets having a maximum value of said difference as said actual imaging wavelength set.

5. The blood information measuring apparatus according to claim 1, wherein said processor determines a blood vessel area from said image signal, calculates density of said blood vessels in said blood vessel area independently from one of said wavelength sets to another, and chooses one of said wavelength sets having a maximum value of said density as said actual imaging wavelength set.

6. The blood information measuring apparatus according to claim 1, wherein said processor calculates a mean value of said oxygen saturation level independently from one of said wavelength sets to another, and chooses one of said wavelength sets having a maximum value of said mean value as said actual imaging wavelength set.

7. The blood information measuring apparatus according to claim 1, wherein said processor applies a binning process to said image signal obtained in said preliminary imaging operation.

8. The blood information measuring apparatus according to claim 1, wherein said processor detects said location of said body portion in said body cavity by an image recognition technique.

9. The blood information measuring apparatus according to claim 1, wherein if said processor detects that said body portion is in an esophagus or a large intestine, said superficial layer wavelength set is chosen as said abnormality detection wavelength set, and if said processor detects that said body portion is in a stomach, said middle layer wavelength set is chosen as said abnormality detection wavelength set.

10. The blood information measuring apparatus according to claim 1, wherein said light source emits white light having a broad wavelength band as said illumination light, and said wavelength tunable element is disposed in said light source to narrow a wavelength band of said illumination light.

11. The blood information measuring apparatus according to claim 1, wherein said light source emits white light having a broad wavelength band as said illumination light, and said wavelength tunable element is disposed in said imaging device to narrow a wavelength band of said reflected light from said body portion irradiated with said illumination light.

12. The blood information measuring apparatus according to claim 1, wherein said processor switches between a normal mode and a special mode according to an input from a mode switch, and wherein in said normal mode, white light having a broad wavelength band is applied to said body portion, and an image produced from said image signal obtained under said white light is displayed on said monitor; and in said special mode, said preliminary imaging operation and said actual imaging operation are carried out, and said image of said body portion is colored based on an oxygen saturation level of each pixel obtained in said actual imaging operation, and said colored image is displayed on said monitor.

13. A blood information measuring method comprising:

applying illumination light to a body portion having a blood vessel;

performing photoelectric conversion of reflected light from said body portion irradiated with said illumination light and outputting an image signal;

narrowing a wavelength band of said illumination light to be applied to said body portion or said reflected light to be incident on an imaging section in accordance with one of a superficial layer wavelength set having a plurality of types of narrow band light in a blue wavelength band, a middle layer wavelength set having a plurality of types of narrow band light in a green wavelength band and a deep layer wavelength set having a plurality of types of narrow band light in a red wavelength band;

calculating oxygen saturation information based on said image signal;

carrying out a preliminary imaging operation to capture a preliminary image of said body portion in each of said wavelength sets by automatically switching among said superficial layer wavelength set, said middle layer wavelength set and said deep layer wavelength set;

automatically choosing one of said wavelength sets as an actual imaging wavelength set to be used in actual imaging operation by analyzing a pattern of hypoxic and hyperoxic regions of each of said preliminary images, said actual imaging wavelength set corresponding to said preliminary image in which a mixed degree of said hyperoxic region and said hypoxic region is highest among said preliminary images;

carrying out said actual imaging operation with use of said actual imaging wavelength set;

displaying on a monitor said oxygen saturation information measured in said actual imaging operation; and detecting a location of said body portion in a body cavity, said carrying out a preliminary imaging operation comprising choosing one of said superficial layer wavelength set, said middle layer wavelength set and said deep layer wavelength set as an abnormality detection wavelength set in accordance with said location, wherein said choosing one of said wavelength sets starts said preliminary imaging operation if a mean value of said oxygen saturation level obtained with said abnormality detection wavelength set is less than a threshold value.

\* \* \* \* \*